United States Patent [19]
Petersen et al.

[11] Patent Number: 5,558,997
[45] Date of Patent: Sep. 24, 1996

[54] MONOCLONAL ANTIBODIES TO MYCOSPHAERELLA SPECIES

[75] Inventors: Frank P. Petersen, Burlington, N.J.;
Mark D. Clymer, Norristown, Pa.;
Sally A. Miller, Pennsauken, N.J.;
James H. Rittenburg, Perkasie, Pa.; G. David Grothaus, Burlington, N.J.

[73] Assignee: Ciba-Geigy Corporation, Tarrytown, N.Y.

[21] Appl. No.: 311,813

[22] Filed: Sep. 26, 1994

Related U.S. Application Data

[63] Continuation of Ser. No. 955,400, Oct. 1, 1992, abandoned, which is a continuation of Ser. No. 546,341, Jun. 29, 1990, abandoned.

[51] Int. Cl.$^6$ .................... G01N 33/53; G01N 33/569; C07K 16/00; C12P 21/08
[52] U.S. Cl. .................... 435/7.31; 435/7.92; 435/7.94; 435/240.27; 435/70.21; 530/388.5; 530/389.1; 530/391.1; 530/391.3
[58] Field of Search .................... 435/7.31, 7.92, 435/7.94, 240.27, 911, 975, 70.21; 530/388.5, 389.1, 391.1, 391.3

[56] References Cited

U.S. PATENT DOCUMENTS

| | | | |
|---|---|---|---|
| 4,803,155 | 2/1989 | Petersen et al. | 435/7.31 |
| 4,845,197 | 7/1989 | Petersen et al. | 530/388.5 |
| 4,879,217 | 11/1989 | Petersen et al. | 435/7.31 |
| 4,997,764 | 3/1991 | Dalla Favera | 435/70.21 |
| 5,187,064 | 2/1993 | Petersen et al. | 435/7.31 |

FOREIGN PATENT DOCUMENTS

| | | |
|---|---|---|
| 0246615 | 11/1987 | European Pat. Off. . |
| 88/5334 | 3/1989 | South Africa . |

OTHER PUBLICATIONS

Agrios, "Plant Diseases Caused by Fungi", *Plant Pathology*, Academic Press: 263–171 (1978).
American Type Culture Collection, *Catalogue of Strains I*, 15th Edition: 410, 510 (1982).
Eyal et al., "Global Insights into Virulence Frequencies of *Mycosphaerella graminicola*", *Phytopathology*, 75(12): 1456–1462 (1985).
Farr et al., *Fungi on Plants and Plant Products in the United States*, APS Press, St. Paul, Minn: 799–807 (1989).
Fries et al., "Identity of the Fungal Endophyte of Ascophyllum with *Mycosphaerella ascophylli* Established by Means of Fluorescent Antibody Tehcnique", *Botanica Marina*, 21: 409–411 (1978).
Kohler et al., *Nature*, 256: 495–497 (1975).
Littlefield, *Science*, 14: 709–710 (1964).
MacDonald et al., "Detection of Low-$M_r$ Glycoproteins in Surface Washes of Some Fungal Cultures by Gel-filtration HPLC and by Monoclonal Antibodies", *J. Gen. Microbiol.* 135: 375–383 (1989).
Maurer et al., "Proteins and Polypeptides as Antigens", *Methods in Enzymology*, 70:49–70 (1980).

Primary Examiner—Marian C. Knode
Assistant Examiner—Patricia A. Duffy
Attorney, Agent, or Firm—James Scott Elmer

[57] ABSTRACT

The invention relates to monoclonal antibodies that react specifically with members of the genus Mycosphaerella and hybridomas that produce such antibodies. The invention is further directed to a method for making a hybridoma cell line that produces monoclonal antibodies that react specifically with at least one species of Mycosphaerella, and a method of obtaining monoclonal antibodies therefrom. Methods and kits for diagnosing Mycosphaerella infections in plant material using such monoclonal antibodies are also within the scope of the invention.

33 Claims, No Drawings

MONOCLONAL ANTIBODIES TO MYCOSPHAERELLA SPECIES

This application is a continuation of application Ser. No.07/955,400, filed Oct. 1, 1992, now abandoned which is a continuation of Ser. No. 07/546,341, filed Jun. 29, 1990, now abandoned.

FIELD OF THE INVENTION

The present invention relates to the field of diagnostic plant pathology. More specifically, the invention relates to monoclonal antibodies useful in the detection of species of the pathogenic fungal genus Mycosphaerella. One of the Mycosphaerella species to which monoclonal antibodies were made, namely *M. graminicola*, is more commonly known by the name of its anamorph (asexual stage) *Septoria tritici*.

BACKGROUND OF THE INVENTION

2.1. Fungal Pathogens

Fungi as a group cause many plant diseases. For purposes of discussion the fungi can be classified as belonging to one of three major taxonomic classes: Basidiomycetes, Phycomycetes, or Ascomycetes.

Basidiomycetes

Members of this class are identified by the presence of a sexual-spore forming structure known as a basidium. Pathogenic forms include smuts, rusts and fleshy species such as mushrooms. Examples include wheat rust, white pine blister, cedar-apple rust, and smuts causing disease in corn, oats, barley, onions and wheat.

Phycomycetes

Members of this class are considered to be more primitive than members of either the Ascomycetes or Basidiomycetes, their distinguishing morphological feature being the absence of mycelial crosswalls. Examples of disease caused by members of the class include the downy mildews of grape and other hosts, root rot and late blight of potato and tomato.

Ascomycetes

Members of this class possess a specialized reproductive structure (an ascus) in which meiosis and sexual spore formation take place. Examples of the more common plant diseases in which Ascomycetes have been identified as the etiologic agent include: powdery mildews on cereals, fruits and many other crops; Dutch elm disease; ergot of grains; peach and plum brown rot; black spot of roses as well as apple scab.

2.2. Mycosphaerella Pathogens

With respect to the present invention, members of the family Dothidiaceae, and particularly the genus Mycosphaerella, are of particular interest. The genus is comprised of over 1,000 species, many of which are plant pathogens of great economic importance. A recent compilation of plant pathogenic fungi in the U.S. lists 258 species of Mycosphaerella as plant pathogens (Farr, D. F., Bills, G. F., Chamuris, G. P. & Rossman, A. 1989, *Fungi on Plant and Plant Products in the United States*, APS Press, Minneapolis: 1252 pp.). The fruiting body of Mycosphaerella is an ostiolate, perithecioid pseudothecium containing eight two-celled ascospores contained in the bitunicate ascus. In many cases the ascospores are the primary mechanism of survival of pathogenic Mycosphaerella species in the absence of a susceptible host plant or under unfavorable environmental conditions. Ascospores often also serve as the primary source of inoculum in a host crop. Many of the species of Mycosphaerella also produce asexual, conidial (anamorph) stages; conidia may be borne in pycnidia, in acervuli, or on free conidiophores. In many instances the conidial stage is most often found in nature. The conidial stage is usually classified separately from the sexual stage on the basis of morphology. Thus, species in the genus Mycosphaerella have conidial stages classified as a number of different genera of Imperfect Fungi. For example, the conidial stage of *M. graminicola* is *Septoria tritici*, while the conidial stage of another Mycosphaerella species, *M. fijiensis*, is *Paracercospora fijiensis*. Several other examples include: *M. musicola* (*Pseudocercospora musae*); *M. fragariae* (*Ramularia brunnea*); *M. pinodes* (*Ascochyta pinodes*); *M. tabifica* (*Phoma betae*); *M. tassiana* (*Cladosporium herbarum*).

The system of classification of asexual stages of ascomycetous fungi is geneally considered to be artificial but continues for practical reasons, since the sexual stages are often difficult to find in nature and may be difficult to induce in pure culture. However, the degree of relatedness of species to one another is reflected in the sexual classification; i.e. two species of Mycosphaerella are likely to be more closely related genetically to one another than two species of Septoria, which are named on the basis of morphological similarities of the asexual stage.

Pathogenic species of Mycosphaerella cause disease on above-ground parts of plants, most often the leaves. Symptoms are lesions that may encompass a large portion of leaf area in irregular or regular patterns, depending on the crop. Some of the most severe and economically damaging diseases worldwide are caused by Mycosphaerella species, and require the use of resistant varieties and/or fungicides for control. *Mycosphaerella fijiensis* and *M. Fijiensis* var. *difformis*, the causal agents of Black Sigatoka (Black Leaf Streak) disease are widespread throughout banana and plantain growing areas of Central America, causing significant economic consequences as a result of yield loss or expenditures for fungicidal control. *Mycosphaerella graminicola*, more commonly known by its asexual stage, *Septoria tritici*, causes significant yield losses in wheat worldwide unless controlled by fungicides or resistant varieties.

Mycosphaerella species may exhibit a latent period of several days to several weeks after infection, in which the pathogen grows in the tissue but symptoms are not produced. Fungicides are most effective in controlling these diseases if applied during the latent period, before significant damage occurs and secondary inocula are produced that will allow the disease to spread. However, routine preventative fungicidal treatments are not usually economically or environmentally justified, and a system that would permit very early detection of these pathogens, preferably during the latent phase of disease development, would be very useful in assuring that fungicides are used appropriately and provide maximal economic benefit. The present invention enables just such a system to be put into practice by providing monoclonal antibodies that are capable of detecting the presence of Mycosphaerella antigens, thus allowing early diagnosis of the disease, and possible prevention of widespread losses to the affected crop.

A number of monoclonal antibodies have now been produced which are capable of identifying various plant pathogens. For example, U.S. Pat. No. 4,845,197 describes monoclonal antibodies which are capable of diagnosing infections caused by fungi in the family Pythiaciae. U.S. Pat. No. 4,803,155 describes monoclonal antibodies which are specific for members of the fungal genus Sclerotinia. U.S.

Pat. No. 4,879,217 discloses monoclonal antibodies which are specific for species of the genus Rhizoctonia.

No previous reports of antibodies having specificity for Mycosphaerella species have been made. Disclosed herein, however, are monoclonal antibodies that react specifically with *M. fijiensis* or *M. graminicola* or which react with more than one Mycosphaerella species, but not with other genera; these monoclonals are particularly useful for specific detection of Mycosphaerella infections on banana and wheat in the early stages of infection before disease symptoms appear.

2.3. Hybridoma Monoclonal Antibody Technology

The use of somatic hybrid cell lines as sources of antibody to individual antigens generally dates from the work of Kohler and Milstein (*Nature*, 256:495–497 (1975)). The antibodies produced are quite different than those recovered from antiserum from conventionally immunized animals. Each hybrid cell line synthesizes a homogeneous immunoglobulin that represents but one of the myriad of types of antibodies that an animal can synthesize in response to an antigen in vivo. Since each immunoglobulin-producing clone is characterized by the single type of antibody it produces, the term monoclonal antibody has been adopted. The advantages of monoclonal antibodies are numerous; they can be obtained in large supply; the preparation is homogeneous with respect to antigen reactivity and remains so over time.

The principle of hybridoma/monoclonal technology is predicated on the observation that when two somatic cells are fused the resultant hybrid displays characteristics of both of the parent cell types. In the case of monoclonal antibody production, the ability to synthesize the particular antibody is derived from an immunocompetent cell (usually a spleen cell) taken from an immunized donor animal, whereas the ability to continuously divide in cell culture is contributed by the other fusion partner, a tumor cell line (often a myeloma). Early fusions were complicated by the fact that myeloma cell line also produced a monoclonal antibody; thus the hybrid often produced two types of monoclonal antibody, one of myeloma origin and the other directed by the genetic information of the immunocompetent cell. Subsequently, tumor cell lines incapable of producing their own monoclonal have been used, e.g., SP2/0-Ag14 or X63-Ag8.653, thereby simplifying the analysis of the resultant fusion products.

Another technical consideration involves the rationale for selecting the successful fusion events (hybrid cells) from the two types of parental cells. Routinely a million or more cells of each type are used in the fusion protocol, and since fusion does not occur with 100% frequency, the job of trying to recover fusion products from the high background of unfused or self-fused parents can be formidable. As mentioned hybridomas are formed by the fusion of short-lived antibody producing (spleen) cells and long-lived myeloma cells. The desired result is a long-lived cell line which produces antibody. Since the spleen cells have a finite life span in culture one can simply wait an appropriate period for all the nonfused or self-fused spleen cells to die; however one must still recover from the resultant population the long-lived antibody producing cells from the long-lived antibody non-producing cells. A popular means for selection hybrid cells is the so-called HAT-selection system. This system involves the use of the enzyme hypoxanthine-guanine-phosphoribosyl transferase (HGPRT). This enzyme functions in the purine salvage pathway in mammalian cells. These cells are also capable of synthesizing purines de novo. Under most conditions, both pathways probably operate to a certain extent. If a cell lacks HGPRT, the salvage pathway is blocked and purines must be manufactured from non-purine materials.

The chemical 8-azaguanine is an antimetabolite which is capable of masquerading as the purine guanine and replacing it in some of its normal reactions. Azaguanine is incorporated into DNA, interfering with the normal growth pattern and leading to cell death. Since azaguanine must be salvaged, any cell which lacks HGPRT activity cannot utilize azaguanine and will grow in its presence.

A selective system which operates on the same enzyme but in the opposite sense in that HGPRT positive cells are selected is described by J. W. Littlefield (*Science*, 145:709 (1964)). It is called HAT and contains hypoxanthine, aminopterin and thymidine (HAT medium). Aminopterin is an antimetabolite that prevents de novo purine synthesis and methylation of deoxyuridylate to form thymidylate. Hypoxanthine can serve as a salvagable purine in the event that aminopterin blocks de novo purine biosynthesis while thymidine bypasses the necessity for the methylation of thymidylate. Thus, in the presence of aminopterin, any cell with positive HGPRT activity will proliferate while cells with negative HGPRT activity will die.

An alternate to the HAT system is the use of HMT medium in place of HAT. HMT employs amethopterin (methotrexate) in place of aminopterin. This method operates on the same principles, but the HMT medium is somewhat less toxic to the growing hybridomas, and therefore the cells can be left on the medium for a longer period of time.

In the hybrid system used for selection in accordance with the present examples, the myeloma cells are resistant to azaguanine and susceptible to amethopterin, that is, they are HGPRT negative. Thus, they will die in the presence of amethopterin. The antibody producing cells are HGPRT positive. By fusing the cells and growing them in HMT medium without azaguanine (HT medium), the successfully fused cells are selected because the myeloma cells which constitute the proliferating line can only grow where HGPRT activity is present and this activity must be supplied by the HGPRT positive cell line. The antibody producing HGPRT positive cell line are not killed in this medium. They will live for a time but will not proliferate.

Thus, by fusing the cells in a HAT or HMT medium, systems are produced in which the myeloma cells and antibody producing cells can grow long enough to produce hybrid cells but in which only the hybrid cells can survive and proliferate. After selection each hybridoma clone is then screened for the ability to produce the particular antibody of interest.

3. SUMMARY OF THE INVENTION

The present invention provides hybridomas that produce monoclonal antibodies that react specifically with members of the genus Mycosphaerella. In a preferred embodiment, these antibodies react with members of the species *Mycosphaerella fijiensis* and/or *Mycosphaerella graminicola*. This should also be noted that the monoclonal antibodies which react with Mycosphaerella are also capable of reacting with antigens from the species' respective asexual stages, e.g., *Septoria tritici* (*M. graminicola*) or *Paracercospora fijiensis* (*M. Fijiensis*); and the stage names are used interchangeably throughout the text and claims. The invention also encompasses specific hybridomas deposited with the ATCC 12301 Parklawn Drive, Rockville, Md. 20852, namely HB 10413 and 10414, which react with more than one species of Mycosphaerella, and HB 10186 which reacts specifically with *Mycosphaerella graminicola*, as well as mutants and variants of each of these cell lines.

The availability of these monoclonal antibodies provides a means for diagnosing Mycosphaerella infections in plant material. Thus, a method for diagnosing such infections is provided which comprises contacting a plant sample suspected of containing antigens of the pathogen of interest with an antibody having specificity for the pathogen, and observing the presence or absence of a reaction between the antibody and antigen present in the sample. In a preferred embodiment, the assay is conducted as a sandwich, or double antibody assay: a first antibody that reacts with the pathogen of interest is contacted with the plant sample, and then a second antibody which also reacts with the pathogen of interest is added, to form an antibody-antigen-antibody complex, if the antigen is present in the sample.

Also provided in this regard are kits for detection of Mycosphaerella which comprise an antibody, preferably immobilized, which reacts with the species of interest, and a detectably labelled antibody which reacts with the species of interest. At least one of the antibodies should be a monoclonal antibody of the present invention, and in certain embodiments, both antibodies may be monoclonals of the present invention.

The invention further provides a method for making a hybridoma cell line that produces monoclonal antibodies that react specifically with at least one species of Mycosphaerella, and a method of obtaining monoclonal antibodies therefrom.

4. DETAILED DESCRIPTION OF THE INVENTION

4.1. Hybridoma Preparation

4.1.1. Antigen Preparation

For preparation of fungal extracts useful in the production of monoclonal antibodies to *Mycosphaerella fijiensis*, either chopped mycelia (or a mixture of chopped mycelia and conidia) of a Mycosphaerella species can be employed as the antigen source. Methods of preparation of such extracts are discussed in detail in Section 5.1.1.

Spore extracts are also capable of yielding antigens which induce antibodies that react with one or more of species Mycosphaerella. Such extracts can be made from *Mycosphaerella graminicola*, either germinated or ungerminated spores, although germinated spores are preferred. The details of the extraction procedure are provided in Section 5.1.2. Distinction between the antibodies so produced is made by a proper screening procedure, also outlined below, in Section 5.1.4. To complete the formulation for inoculation, the antigen extract preferably is combined with an appropriate adjuvant. The adjuvants may be any which are commonly used in the art for this purpose; however, good results have been achieved using Freund's complete adjuvant for the first injection and Freund's incomplete adjuvant for any subsequent injections.

4.1.2. Immunization

The antibodies described in the present examples were made using mice as the antibody source. However, the identity of the experimental animal is not critical, and may be selected from any of the experimental animals commonly used for this purpose, such as rats, rabbits or goats.

The program for inoculation is not critical and may be any normally used for this purpose in the art. Such procedures are described, for example, in Goding, *Monoclonal Antibodies: Principles and Practice*, Academic Press, New York, 1983.

A useful program is one in which a first immunization is given intraperitoneally, of the antigen combined with an appropriate adjuvant. Booster injections can then be administered at two week intervals. Two or more boosters may be given. The animals are tail bled to determine if the serum contains antibodies specific to the antigen of interest. The animal is subsequently sacrificed and the spleen removed to provide a source of lymphocytes.

4.1.3. Fusion

Fusion procedures for creation of hybridomas are well known in the art, and any of the known procedures are useful for the production of hybridomas producing Mycosphaerella-specific monoclonals. The basic procedure used in the present examples is a modification of that developed by Kohler and Milstein (*Nature* 256:495, 1975) and Hammerling (*Eur. J. Immunol.* 7:743, 1977).

To summarize briefly one procedure which has proven effective, spleen cells (or alternately, peripheral blood lymphocytes) are isolated from the immunized animal, and the number of cells counted. T cells used as a feeder layer at a concentration of 10 million cells/10 ml of medium have been employed successfully. An appropriate immortal cell line, preferably a myeloma cell line is selected and added to the lymphocytes in a ratio of about 4:1 lymphocytes:myeloma. A useful cell line is the NS-1 myeloma cell line. At room temperature, PEG (polyethylene glycol) 1500 is added to the combined cells, and then diluted slowly with DMEM. After centrifugation, prewarmed HMT medium is added to the pellet which is resuspended. The sample is further diluted with HMT medium (see Example 1 for composition) and small samples distributed to the wells of a microtiter plate. The plates are then placed in a 9% $CO_2$ incubation with at least 95% humidity. Cells are re-fed with HMT medium after 5–7 days. Clusters of hybridoma cells begin to appear after about 5–7 days. Further feedings are made with HT medium.

4.1.4. Screening

Those hybridomas producing antibodies to Mycosphaerella are identified using prepared fungal material of the particular species of interest, for example, either mycelia, conidia, or germinated spores in an ELISA format. In particular, mycelial material is a useful source from *M. Fijiensis*, while germinated conidia are useful material from *M. graminicola*. Those wells demonstrating positive responses in the ELISA are subcloned to select pure strains of hybridoma cells. The subcloned lines are retested for specific antibody activity to fungal components.

In order to determine the degree of specificity of the selected antibodies, it is desirable to further screen them against a panel of fungal pathogens which may be either related or unrelated to the Mycosphaerella. For example, to obtain a *Mycosphaerella graminicola*-specific antibody the selected antibodies should be tested against other species of Mycosphaerella, as well as against more distantly related or unrelated species.

Examples of primary panels useful for the present purposes is presented in Tables 1 and 4. It is generally recommended to perform screenings in both a single and a double antibody format, as certain antibodies may be useful in one format, but not another.

4.2. Characterization of the Antibodies

A number of antibodies falling within the scope of one or another of the claims have been produced by the procedure. More than one antibody from those initially selected may have been produced by each fusion and screening; however, certain antibodies have been particularly noted, for their high level of specificity and/or their sensitivity in certain assay formats. Among the preferred antibodies for Mycosphaerella identification are those produced by hybridomas Mfl 4C6 and Mfd1 8E6. The hybridoma Mfl 4C6 produces an antibody having a high level of specificity for species of Mycosphaerella, with cross-reactivity observed only with the very distantly related species *Rhizopus stolonifer*. This property does not interfere with the antibodies' utility in detection of Mycosphaerella; moreover, MF14C6 is very sensitive in a double antibody format. The Mfd1 8E6 antibody shows good reactivity with various species of Mycosphaerella, and no cross reactivity with species of other genera. These antibodies are of the IgG1 immunoglobulin subclass.

With regard to *M. graminicola*, specifically the hybridoma Mg37B5 secretes antibodies of the subclass IgG3 which are highly specific and sensitive for *M. graminicola*. However, as can be seen from Table 1, other antibodies having these characteristics have also been produced.

Examples of hybridomas producing each of these types of antibodies have been deposited, under the terms of the Budapest Treaty, with the American Type Culture Collection (ATCC), Rockville, Md., and have been given the following accession numbers:

| Hybridoma | Specificity | Accession No. |
| --- | --- | --- |
| Mf14C6-E8 | Mycosphaerella species | HB 10413 |
| Mf318E6 | Mycosphaerella species | HB 10414 |
| Mg37B5 | *Mycosphaerella graminicola* | HB 10186 |

It is to be understood that the above deposits are made for purposes of exemplification only, and the present claims are not to be construed as being limited thereby. One skilled in the art will readily recognize that similar antibodies can be prepared by repetition of the procedures described above.

4.2.1. Diagnostic Method and Kit

As shown above, the pathogens in question are capable of causing serious damage to those plants which are infested by them, and early diagnosis is therefore highly desirable. The present antibodies now provide a method by which the pathogens can be detected in plant material before any visible symptoms of the disease appear on the plant.

The antibodies described above may be used as the basic reagents of a number of different immunoassays to determine the presence of a particular species in plant material. Generally speaking, the antibodies can be employed in any type of immunoassay, whether qualitative or quantitative. This includes both single site and two-site, or sandwich, assays of the non-competitive type, as well as in traditional competitive binding assays.

Particularly preferred, for ease of detection, and its quantitative nature, is the sandwich or double antibody assay, of which a number of variations exist, all of which are intended to be encompassed by the present invention.

For example, in a typical forward assay, unlabeled antibody is immobilized on a solid substrate and the sample to be tested brought into contact with the bound molecule. After a suitable period of incubation, for a period of time sufficient to allow formation of an antibody-antigen binary complex, a second antibody, labelled with a reporter molecule capable of inducing a detectable signal, is then added and incubated, allowing time sufficient for the formation of a ternary complex of antibody-antigen-labeled antibody. Any unreacted material is washed away, and the presence of the antigen is determined by observation of a signal, or may be quantitated by comparing with a control sample containing known amounts of antigen. Variations on the forward assay include the simultaneous assay, in which both sample and antibody are added simultaneously to the bound antibody, or a reverse assay in which the labelled antibody and sample to be tested are first combined, incubated and added to the unlabelled surface bound antibody. These techniques are well known to those skilled in the art, and the possibility of minor variations will be readily apparent. As used herein, "sandwich assay" is intended to encompass all variations on the basic two-site technique.

For the immunoassays of the present invention, the only limiting factor is that at least one antibody has the required specificity. Thus, a number of possible combinations are possible. For example, one antibody may be polyclonal, and the other monoclonal. Alternately, one antibody may be a general antibody, which binds both the pathogen of interest and other fungi, while the second antibody is specific for the pathogen of interest. Also, both antibodies may be specific for the pathogen of interest.

As a more specific example, in a typical forward sandwich assay, a general Mycosphaerella-binding antibody is either covalently or passively bound to a solid surface. The solid surface is usually glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art. Following binding, the solid phase-antibody complex is washed in preparation for the test sample. An aliquot of the plant extract to be tested is then added to the solid phase complex and incubated at 25° C., for a period of time sufficient to allow binding of any Mycosphaerella present to the antibody. The incubation period will vary, but will generally be in the range of about 2 minutes-16 hours. Following the incubation period, the antibody-Mycosphaerella solid phase is washed and dried, incubated with a second antibody specific for Mycosphaerella. The second antibody is linked to a reporter molecule, the visible signal of which is used to indicate the binding of the second antibody to any antigen in the sample By "reporter molecule", as used in the present specification and claims, is meant a molecule which by its chemical nature, provides an analytically detectable signal which allows the detection of antigen-bound antibody. Detection must be at least relatively quantifiable, to allow determination of the amount of antigen in the sample, this may be calculated in absolute terms, or may be done in comparison with a standard (or series of standards) containing a known normal level of antigen.

The most commonly used reporter molecules in this type of assay are either enzymes, fluorophores or radionuclide-containing molecules. In the case of an enzyme immunoassay an enzyme is conjugated to the second antibody, often by means of glutaraldehyde or periodate. As will be readily recognized, however, a wide variety of different conjugation techniques exist, which are well-known to the skilled artisan. Commonly used enzymes include horseradish peroxidase, glucose oxidase, β-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or tolidine are commonly used. It is also possible to employ fluorogenic substrates, which yield a fluorescent product rather than the chromogenic substrates noted above. In all cases, the enzyme-labelled antigen-specific antibody is added to the first antibody-Mycosphaerella complex, allowed to bind to the complex, then the excess reagent is washed away. A solution containing the appropriate substrate is then added to the tertiary complex of antibody-antigen-labelled antibody. The substrate reacts with the enzyme linked to the second antibody, giving a qualitative visual signal, which may be further quantitated, usually spectrophotometrically, to give an evaluation of the amount of antigen which is present in the serum sample.

Alternately, fluorescent compounds, such as fluorescein and rhodamine, may be chemically coupled to antibodies without altering their binding capacity. When activated by illumination with light of a particular wavelength, the fluorochrome-labelled antibody absorbs the light energy, inducing a state of excitability in the molecule, followed by emission of the light at a characteristic longer wavelength. The emission appears as a characteristic color visually detectable with a light microscope. As in the EIA, the fluorescent labelled PLF-specific antibody is allowed to bind to the first antibody-ferritin complex. After washing of the unbound reagent, the remaining ternary complex is then exposed to light of the appropriate wavelength, and the fluorescence observed indicates the presence of interest. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

5. EXAMPLES

The following examples illustrate the methods of preparation of the hybridomas and antibodies of the present invention.

5.1. Antigen Preparation

5.1.1. *Mycosphaerella Fijiensis*

Isolates of *Mycosphaerella fijiensis* are concurrently grown on V-8 agar plates. V-8 agar is prepared as follows:

150 ml V-8 juice (non-clarified)

1.5 g calcium carbonate 18.0 g agar 1.0 L distilled water

If the isolate is already on a V-8 agar plate, 7–14 day old plates are flooded with 10 ml of sterile distilled water and conidia dislodged using a sterile cell scraper or glass rod. A small aliquot of the conidial suspension is aseptically removed and observed under the microscope for the presence of typical long and narrow Cercospora-like conidia. 0.1 ml of this suspension is placed onto V-8 agar plates and spread evenly over the surface using a sterile bent glass rod. The plates are incubated (parafilmed) under continuous light at room temperature. Continuous transfers of the isolate may affect pathogenicity over time. Fresh isolates should be revived from liquid nitrogen every 3 months.

Isolates of *Mycosphaerella fijiensis* can be revived from liquid nitrogen by thawing the vial at room temperature and plating agar plugs onto concentrated V-8 agar plates. Plates are incubated at room temperature under continuous light. After visible growth appears on the agar plug (5–7 days), the plug is aseptically removed using sterile forceps and the plug is spread over the surface of V-8 agar plates.

Antigen can be produced using either conidia or chopped mycelium as the inoculant in broth cultures:

Conidial inoculum is prepared as described above using V-8 plates seeded with a conidial suspension. The inoculum plates are incubated at room temperature under continuous light for 7–14 days (10 days is optimal as reported in the literature). Plates are flooded with 10 ml of sterile distilled water and conidia dislodged as described above. 0.1 ml of the suspension is aseptically removed and using a hemacytometer, the number of conidia counted and the conidial concentration adjusted aseptically to 100,000 conidia/ml water. If done aseptically, 0.1 ml of the suspension can be used to seed additional V-8 plates. Previously, conidia numbers ranging from 500,000 to 900,000 could be harvested from a single agar plate.

Mycelial inoculum is prepared by inoculating 250 ml tissue culture flasks (Falcon-3024) containing 50 ml of sterile Phytone-Dextrose broth with either a conidial suspension (100,000 to 200,000 conidia) or mycelial chunks removed from an agar plate. Phytone-Dextrose broth is prepared as follows:

10 g Bacto-Soytone (Phytone)

10 g Dextrose

1 L distilled water.

The flasks are incubated upright for 3 days, then shaken vigorously and laid flat for approx. 5–7 days. After incubation, this suspension is aseptically transferred to a sterile 50 ml Omnimixer chamber. This suspension is ground on high for 30 seconds to thoroughly chop the mycelium.

Aseptically, 200,000 conidia or 0.5 ml of chopped mycelial suspension are added to 50 ml of Phytone-Dextrose broth in a 250 ml flask and incubate with shaking in the water bath at 26° C. and 80 rpm. Incubate the flasks for 8 days.

Mycelium is harvested using coffee filters (6.4×8.3 cm) in a Buchner funnel under vacuum since Mycosphaerella grows in compact spheres in broth cultures which may pass through cheesecloth.

5.1.2. *Mycosphaerella Graminicola*

Antigen extracts can be prepared from either germinated or ungerminated spores, as follows:

5.1.2.1. Ungerminated Spores

Conidia of an isolate of *S. tritici* are streaked out on a CDV8 plate (Czapek-Dox Broth, Difco Cat #0338-01-2, supplemented with "V-8" juice, Campbell's) using an inoculating loop. The plate is placed in 18° C. incubation under near UV light. A 5–7 day old culture is flooded with sterile distilled water and the conidia gently dislodged by rubbing a sterile inoculating loop over the surface of the agar. The number of conidia/ml in the resulting suspension is determined using a hemacytometer (spore concentrations may be very high, a 1:50 dilution is recommended for a cloudy suspension). The spore suspension is aseptically diluted to a final concentration of 2 million conidia/ml with sterile distilled water. Ten 250 ml Ehrlenmeyer flasks containing 50 ml of yeast sucrose medium (YSM) with 1 ml of inoculum each (more flasks are necessary for a production batch) are aseptically inoculated. The YSM inoculated flasks are placed on a shaker (high speed) at 18° C. with ambient light and five of the flasks are harvested after 96 hours. The remaining flasks are used to prepare germinated spores, infra. The contents of the flasks are poured into a 250 ml centrifuge bottle and centrifuged at 3000 rpm for 5 minutes. The supernatant is poured off, and the pellet is washed once with distilled water, and recentrifuged. The pellet is resuspended in 50 ml of PBS and extracted in the Dyno-mil for 15 minutes.

5.1.2.2. Germinated Spores

The five remaining flasks from the procedure described above are harvested after 96 hours and allowed to germinate in water according to the following procedure.

The contents of each flask are aseptically transferred to a sterile Falcon tube and centrifuged at 3000 rpm for 5 min. The supernatant is poured off, washed once with sterile, distilled water, and recentrifuged. The pellet is resuspended completely in 50 ml sterile, distilled water. The suspension in each Falcon tube is transferred to a sterile, 250 ml Erhlenmeyer flask. The inoculated flasks are placed on a shaker (high speed) at 18° C. in ambient light for 72 hours. After 72 hours, the spores are harvested by pouring the contents of 5 flasks into one 250 ml centrifuge bottle (withdraw a 1 ml sample and determine % germination using a hemacytometer). The sample is centrifuged at 3000 rpm for 5 minutes, the supernatant poured off, washed once with distilled water, and recentrifuged. The pellet is resuspended in 50 ml of PBS and extracted in the Dyno-mil for 15 minutes.

5.1.3. Immunization and Fusion

The following description is for the *Mycosphaerella graminicola* immunization, but the Mycosphaerella immunization, using an *M. figiensis* extract, is performed in an identical manner.

The first immunization is done intraperitoneally in a Balb/C mouse with 0.25 ml of Mg3 fungal extract emulsified in 0.25 ml Freund's Complete Adjuvant. Booster injections are performed using the same immunogen in Freund's Incomplete Adjuvant at two week intervals. The fourth injection, third booster, is done with Mg3 fungal extract in incomplete adjuvant followed in two weeks with a booster of the same preparation. The mouse is sacrificed by cervical dislocation on the tenth day and the spleen excised for the extraction of lymphocytes. Prior to sacrifice, the mouse is tail bled and the serum tested for the presence of antibodies specific to the immunogen.

The mouse is sacrificed by cervical dislocation and the spleen surgically removed. The spleen is placed on an 80-mesh sterile screen in a sterile disposable petri dish, cut with a scalpel and massaged with a sterile plunger from a 3 cc syringe. During this procedure, the spleen is rinsed several times with DMEM. The cell suspension is transferred to a sterile 50 ml disposable centrifuge tube. The screen and remaining tissue fragments are washed again with DMEM and the washings added to the tube. The cell suspension is spun down at 2000 rpm for 10 minutes (centrifugations are all at room temperature). The supernatant is decanted and the pellet washed with 4 ml of red blood cell lysing solution (0.83% $NH_4Cl$, 0.01M $KHCO_3$, 0.1 mM EDTA) for 90 seconds at room temperature. The lysing reaction is halted by diluting the contents of the tube to 45 ml with DMEM. The contents are centrifuged again at 2000 rpm for 10 minutes. The supernatant is decanted and the pellet is resuspended in 10 ml DMEM. A sample of the cell suspension is retained for cell counting. The total number of viable cells in the suspension is $2.985\times10^8$ cells.

Myeloma cells (P3NS1/1-Ag4-1 (NS1) obtained from American Type Culture Collection, ATCC #TIB-18) are removed from culture medium by centrifugation in a 50 ml sterile centrifuge tube at 2000 rpm for 10 minutes. The supernatant is decanted and the pellet resuspended in 10 ml DMEM for cell counting. $7.46\times10^7$ myeloma cells are needed to give a 4:1 ratio of spleen cells to myeloma cells. The appropriate amount of myeloma cells are added to the spleen cell suspension. The combined cells are centrifuged at 2000 rpm for 10 minutes. Following centrifugation, the supernatant is decanted.

1 ml PEG 1500 (Boehringer Mannheim Biochemicals, cat. #783-641) at room temperature is added to the pellet. The cells are very gently resuspended with a 2 ml pipet and an automatic pipettor. The cell suspension is diluted very slowly by the addition of 10 ml DMEM dropwise over 10 minutes with the gentle swirling of the tube to keep the cells in suspension. The suspension is then slowly diluted to 45 ml with DMEM and centrifuged 10 minutes at 1500 rpm. The supernatant is decanted, the pellet washed gently with 10 ml DMEM and recentrifuged at 1500 rpm for 10 minutes. The supernatant is decanted and prewarmed HMT medium is added to the tube. The pellet is resuspended, transferred to a disposable sterile culture flask, and diluted further to 80 ml with HMT medium. The final dilution is added to the inner 60 wells each of nine 96 well microtiter plates (Falcon, cat. #3870) using a 10 ml pipet, two drops per well. The outer row of each plate is then filled with DMEM+antibiotics. The microtiter plates are placed in a 9% $CO_2$ incubator with at least 95% humidity.

Cells are refed with HMT medium of the following composition after 5–7 days.

| HMT Medium | Composition |
|---|---|
| DMEM | 70.0 ml |
| L-glutamine | 1.0 ml |
| Penicillin-Streptomycin | 1.0 ml |
| Methotrexate 22.73 mg | 1.0 ml |
| Hypoxanthine/Thymidine | 2.0 ml |
| Fetal Bovine Serum | 20.0 ml |
| Origen-HCF | 5.0 ml |

Clusters of hybridoma cells begin to appear after 5–7 days. Further feedings are made with HT medium, the same composition as HMT medium without methotrexate and Origen-HCF.

5.1.4. Screening for Hybridomas 5.1.4.1. *Mycosphaerella Graminicola*

Hybridomas producing antibodies to fungal pathogens are identified using prepared extract of *Mycosphaerella graminicola* 30% germinated spores (protein concentration 5 μg/ml in carbonate buffer) in an ELISA format. Those wells demonstrating positive response in ELISA's are subcloned so that pure strains of hybridoma cells are selected. The subcloning method involves diluting the cells from one well to<100 cells in 12 ml HT medium with 5% Origin-HCF. This dilute cell suspension is added to a microtiter plate, two drops per well. The wells of the subcloning plate are retested for specific antibody activity to fungal components. Positive wells are then transferred to larger culture vessels for mass culturing.

ELISA—Carbonate Procedure

360 μl of carbonate buffer containing 5 μg/ml antigen is placed into each well of a microtiter plate (Nunc, cat. #8667) and incubated 3 hours at room temperature. The plates are washed 3 times with carbonate buffer. The wells are filled with blocking solution and incubated 30 minutes at room temperature. The remaining solution is shaken out, the plates patted on paper towels and dried overnight at 37° C. in a mechanical convection incubator. The plates are then sealed in foil pouches containing dessicant bags and stored at 4° C.

Plates are removed from storage and allowed to warm to room temperature. 100 μl of supernatant sample is placed into each well and incubated 10 minutes on a microplate shaker at room temperature. The remaining solution is discarded and the plate is washed five times with wash buffer (20 mM Tris, 150 mM NaCl, 0.5% Tween-80, 0.01% Thimerosal, pH 7.8). 100 μl of peroxidase-conjugated goat anti-mouse IgG (KPL, cat. #14-18-02) diluted 1:1000 in 0.1% BSA in PBS is added to each well. Plates are incubated 10 minutes on a shaker at room temperature. The remaining solution is discarded and the plates washed five times with wash buffer. 100 μl of ABTS substrate is placed in each well and the plates are incubated 10 minutes as before. The enzyme/substrate reaction is stopped by adding 50 μl of 1.5% NaF to each well and briefly mixing on the shaker. Absorbance is read at 405 nm.

Required Solutions:

1. Carbonate Buffer: 0.1M carbonate, pH 9.6, consists of 1.56 g/l $Na_2CO_3$ and 2.93 g/l $NaHCO_3$ in DI $H_2O$.
2. PBS: 2.19 g/l $Na_2HPO_4$, 0.56 g/l $NaH_2PO_4$, 8.76 g/l lNaCl in DI $H_2O$, pH 7.2.
3. ABTS Stock: 15 mg/ml 2,2'-Azinobis(3-ethylbenzthiazolinesulfonic acid) in DI $H_2O$.
4. Citrate Buffer: 23 g/l Citric acid, pH 4.5, then add 0.5 ml 30% $H_2O_2$.
5. ABTS Substrate: ABTS stock solution is diluted 1 ml with 24 ml citrate buffer.

All buffer solutions are made with anhydrous reagents when available and DI H$_2$O.

The results of a primary screening of a number of antibodies against a panel of fungal pathogen antigens is shown in Table 1.

TABLE 1

Single antibody screen of *Mycosphaerella gramincola* primary fungal panel against monoclonal antibodies Mg37B5, Mg35D10, Mg39G8, Mg35D6. Microtiter plates were coated with antigen at 5 ug/ml.

| | Isolate | Mg37B5 | Mg35D10 | Mg39G8 | Mg35D6 |
|---|---|---|---|---|---|
| *M. graminicola* | 3G | 2.00+ | 2.00+ | 1.74 | 1.01 |
| *M. graminicola* | 4G | 2.00+ | 1.75 | 1.51 | 0.28 |
| *Leptosphaeria nodorum* | 1 | 0.01 | 0.02 | 0.03 | 0.27 |
| *Pyrenophora tritici-repentis* | 1a | 0.01 | 0.00 | 0.02 | 0.21 |
| Alternaria species | 2 | 0.02 | 0.02 | 0.03 | 1.13 |
| *Apergillus fumigatus* | 1 | 0.01 | 0.00 | 0.01 | 0.24 |
| Epicoccum species | 1 | 0.02 | 0.02 | 0.02 | 1.55 |
| Phoma species | 1 | 0.02 | 0.07 | 0.00 | 1.14 |
| Penicillium species | 15 | 0.01 | 0.01 | 0.03 | 0.37 |
| Cladosporium species | 1 | 0.01 | 0.01 | 0.01 | 0.17 |
| Blank (0.1% 4 BSA in PBS) | 0.01 | 0.01 | 0.03 | 0.18 | |

Single antibody screens were performed using antibody Mg37B5 against an expanded a panel of isolates of related fungal pathogens, as well as against several isolates of *Mycosphaerella graminicola.* The results are shown respectively, in Tables 2 and 3.

TABLE 2

Single antibody screen of *Mycosphaerella graminicola* secondary fungal panel of related and unrelated species against monoclonal antibody Mg37B5. Microtiter plates coated with antigen at 5 ug/ml. NT = Not Tested

| Isolate | No. of Isolates tested | Mg37B5 |
|---|---|---|
| *Mycosphaerella fijiensis* | 3 | 0.015 |
| *Mycosphaerella graminicola* | 5 | 2.00+ |
| *Mycosphaerella graminicola* | 1 | 1.125 |
| *Mycosphaerella musicola* | 3 | 0.014 |
| *M. fijiensis* var. *difformis* | 3 | 0.016 |
| *Alternaria alternata* | 1 | 0.000 |
| Alternaria spp. | 1 | 0.056 |
| Aspergillus spp. | 3 | 0.000 |
| *Aspergillus fumigatus* | 1 | 0.000 |
| *Aspergillus terreus* | 1 | 0.000 |
| *Aspergillus candidis* | 1 | 0.007 |
| Aspergillus varians | 1 | 0.034 |
| *Botrytis alli* | 1 | 0.000 |
| *Botrytis cinerea* | 2 | 0.037 |
| *Bipolaris oryzae* | 2 | 0.016 |
| *Bipolaris sorokiniana* | 3 | 0.000 |
| *Cladosporium cladosporioides* | 1 | 0.048 |
| *Cladosporium herbarum* | 1 | 0.000 |
| *Cladosporium macrocarpum* | 1 | 0.000 |
| *Cladosporium musae* | 1 | 0.023 |
| Cladosporium spp. | 2 | 0.058 |
| Cladosporium spp. | 1 | 0.001 |
| *Colletotrichum graminicola* | 3 | 0.038 |
| Colletotrichum spp. | 1 | 0.089 |
| Colletotrichum spp. | 1 | 0.000 |
| *Curvularia lunata* | 1 | 0.080 |
| *Chloridium musae* | 1 | 0.000 |
| *Cordana musae* | 1 | 0.028 |
| *Dreschlera gigantea* | 1 | 0.000 |
| *Diplodia gossypina* | 1 | 0.001 |
| *Deightoniella torulosa* | 1 | 0.000 |
| Deightoniella spp. | 1 | 0.000 |
| *Epicoccum nigrum* | 1 | 0.049 |

TABLE 2-continued

Single antibody screen of *Mycosphaerella graminicola* secondary fungal panel of related and unrelated species against monoclonal antibody Mg37B5. Microtiter plates coated with antigen at 5 ug/ml. NT = Not Tested

| Isolate | No. of Isolates tested | Mg37B5 |
|---|---|---|
| Epicoccum spp. | 1 | 0.000 |
| *Fusarium oxysporum* | 1 | 0.004 |
| *Fusarium nivale* | 1 | 0.028 |
| Fusarium spp. | 1 | 0.000 |
| *Helminthosporium sativum* | 4 | 0.051 |
| *Leptosphaeria korrae* | 3 | 0.000 |
| *Leptosphaeria nodorum* | 2 | 0.001 |
| *Lambertella subrenispora* | 1 | 0.000 |
| Monilinia spp. | 2 | 0.004 |
| *Mortierella spinosa* | 1 | NT |
| *Myriosclerotinia dennisii* | 1 | 0.112 |
| Penicillium spp. | 5 | 0.017 |
| *Pyrenophora tritici-repentis* | 2 | 0.000 |
| *Pythim aphanidermatum* | 3 | 0.002 |
| Phoma spp. | 1 | 0.000 |
| *Pseudocercosporella herpotrichoides* | 1 | 0.000 |
| *Rhizopus stolonifer* | 4 | 0.006 |
| *Rhizoctonia solani* | 2 | 0.034 |
| *Sclerotinia sclerotiorum* | 2 | 0.026 |
| *Stemphylium vesicarium* | 2 | 0.019 |

TABLE 3

Single antibody screen of *Mycosphaerella graminicola* against monoclonal antibody Mg37B5. Microtiter plates were coated with antigen at 5 ug/ml.

| Antigen | Batch | Moncolonal Antibody Mg37B5 Absorbance (405 nm) |
|---|---|---|
| Mg 3 | 012G | 2.000+ |
| Mg 4 | 011G | 2.000+ |
| Mg 5 | 010G | 2.000+ |
| Mg 7 | 010G | 2.000+ |
| Mg 8 | 010G | 0.559 |

TABLE 3-continued

Single antibody screen of *Mycosphaerella graminicola* against monoclonal antibody Mg37B5. Microtiter plates were coated with antigen at 5 ug/ml.

| Antigen | Batch | Moncolonal Antibody Mg37B5 Absorbance (405 nm) |
|---|---|---|
| Mg 10 | 010G | 2.000+ |
| Mg 15 | 010G | 1.125 |
| Mg 28 | 010G | 2.000+ |
| Mg 40 | 010G | 2.000+ |
| Mg 41 | 010G | 2.000+ |
| Mg 42 | 010G | 2.000+ |
| Mg 43 | 010G | 2.000+ |
| Mg 44 | 010G | 2.000+ |
| Mg 45 | 010G | 2.000+ |

Three cell lines from the *Mycosphaerella graminicola* fusion were tested against the fungal isolates of the primary cross reactivity panel for *Mycosphaerella fijiensis* in a single antibody format. As shown in Table 4, each of these antibodies (all IgG1) shows a strong cross-reactivity with Mycosphaerella species, as well as being capable of reacting with *Mycosphaerella graminicola*.

TABLE 4

Single antibody screen of *Mycosphaerella fijiensis* primary fungal panel against monoclonal antibodies Mg39G8, Mg35D10, and Mg35D3. Microtiter plates were coated with antigen at 5 ug/ml.

| | Isolate | Mg39G8 | Mg35D10 | Mg35D3 |
|---|---|---|---|---|
| *Mycosphaerella fijiensis* | 1 | 1.30 | 0.74 | 0.80 |
| *M. fijiensis* var. *difformis* | 1 | 0.07 | 0.27 | 0.37 |
| *M. fijiensis* var. *difformis* | 3 | 1.66 | 1.83 | 1.89 |
| *Mycosphaerella musicola* | 1 | 1.30 | 1.56 | 1.80 |
| *Mycosphaerella graminicola* | 3G | 1.55 | 1.33 | 1.61 |
| *Deightoniella torulosa* | 1 | 0.00 | 0.02 | 0.08 |
| *Cladosporium herbarum* | 1 | 0.00 | 0.03 | 0.06 |
| *Dreschlera gigantea* | 1 | 0.00 | 0.00 | 0.03 |
| *Cladosporium cladosporioides* | 1 | 0.00 | 0.00 | 0.03 |
| *Cladosporium musae* | 1 | 0.01 | 0.03 | 0.08 |
| *Rhizopus stolonifer* | 2 | 0.00 | 0.00 | 0.03 |

The monoclonal antibody of hybridoma Mg37B5 and other monoclonals, was further tested in a double antibody format against an infected wheat, and other comparative material, as follows:

Monoclonal antibodies are purified from hybridoma supernatant samples by Protein A affinity chromatography. The eluant from the chromatography column is dialyzed against two changes of PBS, >100 volumes per dialysis cycle. The protein concentration of the antibody solution is calculated by dividing the absorbance of the solution at 280 nm by 1.4 to give the concentration in milligrams of protein per milliliter.

Microtiter plates are sensitized by first diluting the purified antibody solution in the appropriate sensitization buffer and then placing 100 µl in each well. The concentration of antibody following dilution is 5 µg/ml in each of three sensitization buffers; Carbonate Buffer, pH 9.6, PBS, ph 7.2 and 0.1M Glycine-HCl, pH 4.5. The microtiter plates are incubated 3 hours at room temperature. The remaining solution is discarded and the wells are washed 3 times with the same buffer as that used for sensitization. The wells are filled with blocking solution and incubated 30 minutes at room temperature. The remaining solution is discarded, the plates blotted on paper towels and then dried at 37° C. overnight in a mechanical convection incubator. The plates are then sealed in foil bags containing a small dessicant pouch and stored at 4° C.

Plates are removed from storage and allowed to equilibrate at room temperature. Antigen solutions are prepared by diluting fungal culture extracts in 0.1% BSA/PBS or by grinding infected wheat leaves in the same buffer. 100 µl of the antigen solution is added to each well and the plates are incubated 10 minutes at room temperature on a microtiter plate shaker. The remaining solution is discarded and the plates are washed 5 times with wash buffer. 100 µl of peroxidase-conjugated sheep anti-Mg3G (0.5 µg/ml in 0.1% BSA/PBS) is added to each well. The plates are incubated as before. The remaining conjugate solution is discarded and the plates washed 5 times with wash buffer. 100 µl of ABTS [2,2'-Azinobis (3-ethyl-benzthiazoline sulfonic acid)]substrate is added to each well and the plates are incubated as before. The color reaction is stopped after 10 minutes by adding 50 µl of 1.5% NaF to each well and mixing briefly on the plate shaker. The absorbance of each well is read at 405 nm.

The results, which are shown in Table 5, indicate that the monoclonals of Mg37B5 are effective in detecting *Mycosphaerella graminicola* in infected plant material.

TABLE 5

Double antibody test using supernatant of cell line Mg37B5 as the capture antibody (concentration of antibody 5 ug/ml, diluent carbonate buffer pH 9.6). Conjugate used was sheep anti-*Mycosphaerella graminicola*. The antigens tested were wheat infected with *Mycosphaerella graminicola*, healthy wheat, and Mg3G isolate.

| Antigen | Mg37B5 |
|---|---|
| *Mycosphaerella graminicola* infected wheat dilution 1:10 | 0.78 |
| Healthy wheat | 0.02 |
| *Mycosphaerella graminicola* isolate 3G 10 ug/ml | 2.0+ |
| 0.1% Bovine Serum Albumin | 0.01 |

5.1.4.2. *Mycosphaerella Fijiensis*

The screening of hybridomas resulting from *Mycosphaerella fijiensis* fusions was performed in substantially the same manner as described for *Mycosphaerella graminicola*, supra. The results of the primary screening panel are shown in Table 6.

TABLE 6

Single antibody screen of *Mycosphaerella fijiensis* primary fungal panel against monoclonal antibodies Mfl4C6, Mfl8E6, Mfd12C3, Mfd13F9, Mfd16D8, Mfd11B9, Mfd18C11 and Mfd17D10. Microtiter plates were coated with antigen at 5 ug/ml. NT = Not Tested.

|  | Mfl 4C6 | Mfd1 8E6 | Mfd1 2C3 | Mfd1 3F9 | Mfd1 6D8 | Mfd1 1B9 | Mfd1 8C11 | Mfd1 7D10 |
|---|---|---|---|---|---|---|---|---|
| *Mycosphaerella fijiensis* | 0.21 | 2.00+ | 2.0+ | 0.08 | 0.02 | 0.69 | 0.79 | 1.64 |
| *M. fijiensis* var. *difformis* | 0.12 | 2.00+ | 2.0+ | 0.49 | 0.82 | 1.65 | 0.61 | 1.83 |
| *M. fijiensis* var. *difformis* | 0.07 | 2.00+ | 2.0+ | 0.09 | 0.06 | 0.00 | 0.36 | 0.95 |
| *Mycosphaerella musicola* | 0.00 | 2.00+ | 2.0+ | 0.09 | 0.04 | 0.21 | 0.55 | 1.74 |
| *Mycosphaerella graminicola* | 0.00 | 1.05 | 0.82 | 0.09 | 0.05 | 0.01 | 0.28 | 0.11 |
| *Deightoniella torulosa* | 0.00 | 0.21 | 0.18 | 0.08 | 0.10 | 0.00 | 0.64 | 0.00 |
| *Cladosporium herbarum* | 0.00 | 0.00 | 0.02 | 0.00 | 0.01 | 0.00 | 0.12 | 0.27 |
| *Dreschlera gigantea* | 0.00 | 0.00 | 0.01 | 0.04 | 0.00 | 0.00 | 0.07 | 0.00 |
| *Cladosporium musae* | 0.00 | 0.00 | 0.08 | 0.06 | 0.02 | 0.00 | 0.03 | 0.00 |
| *Fusarium oxysporium* | 0.00 | 0.00 | 0.04 | 0.08 | 0.00 | 0.00 | 0.05 | 0.00 |
| *Rhizopus stolonifer* | 0.02 | 0.05 | 0.12 | 0.07 | NT | 0.00 | 0.60 | 0.00 |
| Blank | 0.00 | 0.00 | 0.06 | 0.09 | NT | 0.00 | 0.00 | 0.00 |

The results of a single antibody assay testing cross reactivity of several Mycosphaerella antibodies against a broad panel of related and unrelated isolates is provided in Tables 7 and 7a. The reactivity of these monoclonal antibodies with multiple isolates of *M. fijiensis* is shown in Tables 8 and 8a.

TABLE 7

Single antibody screen of *Mycosphaerella fijiensis* secondary fungal panel against monoclonal antibodies Mf 14C6, Mf18E6, Mfd12C3 and Mfd17D10. Microtiter plates were coated with antigen at 5 ug/ml. NT = Not Tested.

| Isolates | Number of Isolates tested | Monoclonal Antibodies | | | |
|---|---|---|---|---|---|
| | | 4C6 | 8E6 | 2C3 | 7D10 |
| *Mycosphaerella fijiensis* | 3 | 0.008 | 2.00+ | 2.00+ | 1.443 |
| *M. fijiensis* var. *difformis* | 3 | 0.041 | 2.00+ | 2.00+ | 0.959 |
| *Mycosphaerella gramincola* | 5 | 0.080 | 0.259 | 0.167 | 0.062 |
| *Mycosphaerella musicola* | 3 | 0.021 | 2.00+ | 1.768 | 0.940 |
| *Alternaria alternata* | 1 | 0.000 | 0.006 | 0.000 | 0.000 |
| Alternaria spp. | 1 | 0.044 | 0.023 | 0.000 | 0.018 |
| Aspergillus spp. | 3 | 0.002 | 0.022 | 0.000 | 0.015 |
| *Aspergillus terreus* | 1 | 0.000 | 0.048 | 0.009 | 0.000 |
| *Aspergillus candidis* | 1 | 0.017 | 0.100 | 0.000 | 0.000 |
| *Aspergillus varians* | 1 | 0.007 | 0.028 | 0.000 | 0.000 |
| *Botrytis allii* | 1 | 0.000 | 0.039 | 0.011 | 0.000 |
| *Botrytis cinerea* | 2 | 0.014 | 0.023 | 0.004 | 0.016 |
| *Bipolaris oryzae* | 2 | 0.071 | 0.033 | 0.031 | 0.054 |
| *Bipolaris sorokiniana* | 3 | 0.000 | 0.004 | 0.000 | 0.008 |
| *Cladosporium cladosporioides* | 1 | 0.000 | 0.000 | 0.000 | 2.00+ |
| *Cladosporium herbarum* | 1 | 0.000 | 0.027 | 0.000 | 2.00+ |
| *Cladosporium macrocarpum* | 1 | 0.000 | 0.079 | 0.000 | 0.000 |
| *Cladosporium musae* | 1 | 0.021 | 0.077 | 0.000 | 0.000 |
| Cladosporium spp. | 2 | 0.027 | 0.015 | 0.002 | 2.00+ |
| Cladosporium spp, | 1 | 0.000 | 0.015 | 0.000 | 0.022 |
| *Colletotrichum graminicola* | 3 | 0.030 | 0.004 | 0.000 | 1.443 |
| Colletotrichum spp. | 1 | 0.000 | 0.012 | 0.003 | 2.00+ |
| Colletotrichum spp. | 1 | 0.000 | 0.045 | 0.000 | 0.646 |
| *Curvularia lunata* | 1 | 0.015 | 0.000 | 0.000 | 0.006 |
| *Chloridium musae* | 1 | 0.000 | 0.005 | 0.034 | 1.254 |
| *Cordana musae* | 1 | 0.000 | 0.037 | 0.002 | 0.021 |
| *Dreschlera gigantea* | 1 | 0.000 | 0.000 | 0.000 | 0.000 |
| *Diplodia gossypina* | 1 | 0.000 | 0.061 | 0.010 | 0.017 |
| *Deightoniella torulosa* | 1 | 0.000 | 0.000 | 0.000 | 0.000 |
| Deightoniella spp. | 1 | 0.000 | 0.028 | 0.012 | 0.000 |
| *Epicoccum nigrum* | 1 | 0.036 | 0.017 | 0.000 | 0.028 |
| Epicoccum spp. | 1 | 0.000 | 0.028 | 0.015 | 0.033 |
| *Fusarium oxysporum* | 1 | 0.016 | 0.067 | 0.012 | 0.017 |
| *Fusarium nivale* | 1 | 0.016 | 0.029 | 0.010 | 2.00+ |
| Fusarium spp. | 1 | 0.000 | 0.015 | 0.016 | 0.040 |
| *Helminthosporium sativum* | 4 | 0.004 | 0.038 | 0.026 | 0.009 |
| *Leptospheria korrae* | 3 | 0.000 | 0.014 | 0.012 | 0.003 |
| *Leptospheria nodorum* | 2 | 0.002 | 0.010 | 0.035 | 0.011 |
| *Lambertella subrenispora* | 1 | 0.022 | 0.001 | 0.000 | 0.000 |
| Monilinia spp. | 2 | 0.000 | 0.044 | 0.021 | 0.025 |
| *Mortierella spinosa* | 1 | NT | 0.000 | 0.000 | 0.000 |
| *Mortierella epigama* | 1 | 0.000 | 0.000 | 0.000 | 0.000 |
| *Myriosclerotinia dennisii* | 1 | 0.000 | 0.060 | 0.014 | 0.050 |
| Penicillium spp. | 5 | 0.017 | 0.183 | 0.119 | 0.003 |
| *Pyrenophora tritici-repentis* | 2 | 0.004 | 0.042 | 0.008 | 0.012 |
| *Pythium aphanidermatum* | 3 | 0.000 | 0.019 | 0.000 | 0.000 |
| Phoma spp. | 1 | 0.000 | 0.095 | 0.007 | 0.023 |
| *Rhizopus stolonifer* | 4 | 0.007 | 0.194 | 0.140 | 0.008 |
| *Rhizoctonia solani* | 2 | 0.007 | 0.029 | 0.011 | 0.000 |
| *Sclerotinia sclerotiorum* | 2 | 0.000 | 0.006 | 0.000 | 0.004 |

TABLE 7a

Single antibody screen of *Mycosphaerella fijiensis* secondary fungal panel against monoclonal antibody Mfd13F9, Mfd16D8, Mfd11B9, Mfd18C11. Microtiter plates were coated with antigen at 5 ug/ml. NT = Not Tested.

| Isolates | Number of Isolates tested | 3F9 | 6D8 | 1B9 | 8C11 |
|---|---|---|---|---|---|
| Mycosphaerella fijiensis | 3 | 0.014 | 0.000 | 0.022 | 0.893 |
| M. fijiensis var. difformis | 3 | 0.088 | 0.134 | 0.091 | 0.688 |
| Mycosphaerella graminicola | 5 | 0.012 | 0.057 | 0.030 | 0.153 |
| Mycosphaerella musicola | 3 | 0.043 | 0.027 | 0.047 | 0.999 |
| Alternaria alternata | 1 | 0.018 | 0.026 | 0.003 | 0.088 |
| Alternaria spp. | 1 | 0.000 | 0.000 | 0.000 | 0.058 |
| Aspergillus spp. | 3 | 0.013 | 0.006 | 0.000 | 0.104 |
| Aspergillus fumigatus | 1 | 0.009 | 0.013 | 0.000 | 0.177 |
| Aspergillus terreus | 1 | 0.000 | 0.000 | 0.000 | 0.075 |
| Aspergillus candidis | 1 | 0.000 | 0.020 | 0.000 | 0.205 |
| Aspergillus varians | 1 | 0.000 | 0.000 | 0.000 | 0.098 |
| Botrytis allii | 1 | 0.000 | 0.000 | 0.000 | 0.156 |
| Botrytis cinerea | 2 | 0.000 | 0.040 | 0.033 | 0.072 |
| Bipolaris oryzae | 2 | 0.004 | 0.000 | 0.000 | 0.438 |
| Bipolaris sorokiniana | 3 | 0.035 | 0.075 | 0.017 | 0.169 |
| Cladosporium cladosporioides | 1 | 0.009 | 0.006 | 0.000 | 0.078 |
| Cladosporium herbarum | 1 | 0.032 | 0.004 | 0.026 | 0.004 |
| Cladosporium macrocarpum | 1 | 0.009 | 0.000 | 0.000 | 0.139 |
| Cladosporium musae | 1 | 0.027 | 0.006 | 0.000 | 0.148 |
| Cladosporium spp. | 2 | 0.053 | 0.145 | 0.148 | 0.014 |
| Cladosporium ssp, | 1 | 0.057 | 0.096 | 0.185 | 0.188 |
| Colletotrichum graminicola | 3 | 0.008 | 0.003 | 0.000 | 0.197 |
| Colletotrichum spp. | 1 | 0.021 | 0.000 | 0.013 | 0.129 |
| Colletotrichum spp. | 1 | 0.003 | 0.003 | 0.004 | 0.101 |
| Curvularia lunata | 1 | 0.014 | 0.000 | 0.000 | 0.082 |
| Chloridium musae | 1 | 0.012 | 0.000 | 0.000 | 0.062 |
| Cordana musae | 1 | 0.000 | 0.009 | 0.000 | 0.068 |
| Dreschlera gigantea | 1 | 0.000 | 0.000 | 0.000 | 0.076 |
| Diplodia gossypina | 1 | 0.043 | 0.002 | 0.002 | 0.059 |
| Deightoniella torulosa | 1 | 0.013 | 0.000 | 0.000 | 0.330 |
| Deightoniella spp. | 1 | 0.000 | 0.000 | 0.000 | 0.316 |
| Epicoccum nigrum | 1 | 0.076 | 0.000 | 0.000 | 0.272 |
| Epicoccum spp. | 1 | 0.089 | 0.170 | 0.142 | 0.183 |
| Fusarium oxysporum | 1 | 0.007 | 0.000 | 0.221 | 0.120 |
| Fusarium nivale | 1 | 0.007 | 0.000 | 0.000 | 0.219 |
| Fusarium spp. | 1 | 0.000 | 0.000 | 0.000 | 0.317 |
| Helminthosporium sativum | 4 | 0.005 | 0.000 | 0.001 | 0.082 |
| Leptospheria korrae | 3 | 0.079 | 0.017 | 0.000 | 0.160 |
| Leptospheria nodorum | 2 | 0.022 | 0.019 | 0.000 | 0.109 |
| Lambertella subrenispora | 1 | 0.023 | 0.000 | 0.007 | 0.239 |
| Monilinia spp. | 2 | 0.470 | 0.009 | 0.024 | 0.053 |
| Mortierella spinosa | 1 | 0.000 | 0.000 | 0.000 | 0.816 |
| Mortierella epigama | 1 | 0.015 | 0.021 | 0.002 | 0.195 |
| Myriosclerotinia dennisii | 1 | 0.000 | 0.000 | 0.000 | 0.793 |
| Penicillium spp. | 5 | 0.010 | 0.004 | 0.000 | 0.261 |
| Pyrenophora tritici-repentis | 2 | 0.390 | 0.015 | 0.007 | 0.149 |
| Pythium aphanidermatum | 3 | 0.067 | 0.002 | 0.006 | 0.387 |
| Phoma spp. | 1 | 0.057 | 0.129 | 0.025 | 0.232 |
| Rhizopus stolonifer | 4 | 0.076 | 0.006 | 0.047 | 0.362 |
| Rhizoctonia solani | 2 | 0.030 | 0.034 | 0.004 | 0.453 |
| Sclerotinia sclerotiorum | 2 | 0.006 | 0.003 | 0.000 | 0.068 |

TABLE 8

Single antibody screen of *Mycosphaerella fijiensis* (Mf), *M. fijiensis* var. *difformis* (Mfd) and *M. musicola* (Mm) against monoclonal antibodies Mf14C6, Mf18E6, Mfd12C3, and Mfd17D10. Microtiter plates were coated with antigen at 5 ug/ml.

| | | Monoclonal Antibody | | | |
|---|---|---|---|---|---|
| Antigen | Batch | Mf14C6 | Mf18E6 Absorbance (405 nm) | Mfd2C3 | Mfd7D10 |
| Mf 1 | 012 | 0.016 | 2.00+ | 2.00+ | 1.654 |
| Mf 2 | 010 | 0.011 | 2.00+ | 2.00+ | 2.00+ |
| Mf 4 | 010 | 0.000 | 2.00+ | 2.00+ | NT |
| Mfd 1 | 010 | 0.002 | 2.00+ | 2.00+ | 1.217 |
| Mfd 2 | 010 | 0.082 | 2.00+ | 2.00+ | 0.657 |
| Mfd 3 | 010 | 0.039 | 2.00+ | 2.00+ | 1.006 |
| Mm 1 | 010 | 0.026 | 2.00+ | 2.00+ | 1.396 |
| Mm 2 | 010 | 0.015 | 2.00+ | 2.00 | 1.040 |
| Mm 3 | 010 | 0.023 | 2.00+ | 1.305 | 0.384 |

TABLE 8a

Single antibody screen of *Mycosphaerella fijiensis* (Mf), *M. fijiensis* var. *difformis* (Mfd) and *M. musicola* (Mm) against monoclonal antibodies Mfd13F9, Mfd16D8, Mfd11B9, Mfd18C11. Microtiter plates were coated with antigen at 5 ug/ml.

| | | Monoclonal Antibody | | | |
|---|---|---|---|---|---|
| Antigen | Batch | Mfd 3F9 | Mfd 6D8 Absorbance (405 nm) | Mfd 1B9 | Mfd 8C11 |
| Mf 1 | 012 | 0.017 | 0.000 | 0.023 | 0.328 |
| Mf 2 | O11 | 0.000 | 0.000 | 0.048 | 0.350 |
| Mf 4 | 010 | 0.025 | 0.009 | 0.000 | 2.000 |
| Mfd 1 | 010 | 0.228 | 0.377 | 0.257 | 0.146 |
| Mfd 2 | 010 | 0.004 | 0.000 | 0.000 | 0.253 |
| Mfd 3 | 010 | 0.032 | 0.025 | 0.015 | 1.666 |
| Mm 1 | 010 | 0.000 | 0.000 | 0.000 | 2.00+ |
| Mm 2 | 010 | 0.021 | 0.007 | 0.000 | 0.370 |
| Mm 3 | 010 | 0.109 | 0.074 | 0.141 | 0.627 |

A double antibody screen of *Mycosphaerella fijiensis* monoclonal antibody Mf14C6 against a broad panel of related and unrelated fungal pathogens is shown in Table 9. This table illustrates both the high level of specificity of the Mf14C6 antibody and the greater sensitivity of the Mf14C6 in a double antibody versus a single antibody screen. Table 10 shows results of double antibody screen at Mf14C6 against a panel of *Mycosphaerella fijiensis* infected banana leaves, and pure culture of *Mycosphaerella fijiensis* as well as healthy banana leaves.

TABLE 9

Double antibody screen of *Mycosphaerella fijiensis* secondary fungal panel against monoclonal antibody Mf14C6. Microtiter plates were coated with Mf14C6 at 5 ug/ml. Second immunoreagent is sheep anti-Mf1 conjugated to horse radish peroxidase. Sheep conjugate used at 5 ug/ml. NT = Not Tested.

| Isolates | Number of Isolates tested | 4C6 |
|---|---|---|
| Mycosphaerella graminicola | 6 | 0.02 |
| Mycosphaerella fijiensis | 3 | 2.00+ |
| Mycosphaerella musicola | 3 | 2.00+ |
| M. fijiensis var. difformis | 3 | 2.00+ |
| Alternaria alternata | 1 | 0.00 |
| Alternaria spp. | 1 | 0.01 |
| Aspergillus spp. | 3 | 0.02 |
| Aspergillus fumigatis | 1 | 0.00 |

TABLE 9-continued

Double antibody screen of *Mycosphaerella fijiensis* secondary fungal panel against monoclonal antibody Mf14C6. Microtiter plates were coated with Mf14C6 at 5 ug/ml. Second immunoreagent is sheep anti-Mf1 conjugated to horse radish peroxidase. Sheep conjugate used at 5 ug/ml. NT = Not Tested.

| Isolates | Number of Isolates tested | 4C6 |
|---|---|---|
| Aspergillus terreus | 1 | 0.00 |
| Aspergillus candidis | 1 | 0.01 |
| Aspergillus varians | 1 | 0.01 |
| Botrytis allii | 1 | 0.04 |
| Botrytis cinerea | 3 | 0.03 |
| Bipolaris oryzae | 2 | 0.01 |
| Bipolaris sorokiniana | 3 | 0.01 |
| Cladosporium cladosporioides | 1 | 0.08 |
| Cladosporium herbarum | 1 | 0.13 |
| Cladosporium macrocarpum | 1 | 0.01 |
| Cladosporium musae | 1 | NT |
| Cladosporium spp. | 2 | 0.04 |
| Cladosporium spp, | 1 | 0.00 |
| Colletotrichum graminicola | 3 | 0.04 |
| Colletotrichum spp. | 1 | 0.00 |
| Curvularia lunata | 1 | 0.00 |
| Chloridium musae | 1 | 0.00 |
| Cordana musae | 1 | 0.00 |
| Dreschlera gigantea | 1 | 0.00 |
| Dipodia gossypina | 1 | 0.00 |
| Deightoniella torulosa | 1 | 0.00 |
| Deightoniella spp. | 1 | 0.01 |
| Epicoccum nigrum | 1 | 0.00 |
| Epicoccum spp. | 1 | 0.00 |
| Fusarium oxysporum | 1 | 0.03 |
| Fusarium nivale | 1 | 0.00 |
| Fusarium spp. | 1 | 0.00 |
| Helminthosporium sativum | 4 | 0.02 |
| Leptospheria korrae | 2 | 0.06 |
| Leptospheria nodorum | 2 | 0.00 |
| Lambertella subrenispora | 1 | 0.01 |
| Monilinia spp. | 2 | 0.09 |
| Mortierella epigama | 1 | 0.03 |
| Myriosclerotinia dennisii | 1 | 0.00 |
| Penicillium spp. | 6 | 0.04 |
| Pyrenophora tritici-repentis | 3 | 0.04 |
| Pythium aphanidermatum | 2 | 0.02 |
| Phoma spp. | 1 | 0.00 |
| Rhizopus stolonifer | 2 | 1.43 |
| Rhizoctonia solani | 3 | 0.00 |
| Sclerotinia sclerotiorum | 2 | 0.01 |

TABLE 10

Double antibody test using supernatant of cell line M14C6 as the capture antibody (concentration of antibody (concentration of antibody 5 ug/ml, diluent carbonate buffer pH 9.6). Conjugate used was sheep anti-*Mycosphaerella fijiensis* (concentration 5 ug/ml, diluent 0.1% BSA/PBS). Antigens used were pure culture of *Mycosphaerella fijiensis*, banana leaves infected with *Mycosphaerella fijiensis* and healthy banana leaves.

| Antigen | Mf14C6 |
|---|---|
| *Mycosphaerella fijiensis* | |
| infected banana leaves | |
| flecked (light infected) | 0.045 |
| spotted (heavily infected) | 1.289 |
| Healthy banana leaves | 0.000 |
| *Mycosphaerella fijiensis* | |
| isolate 10 ug/ml | 2.00+ |
| 0.1% Bovine Serum Albumin | 0.000 |

What we claim is:

1. A hybridoma cell line that produces a monoclonal antibody which binds with at least one species of Mycosphaerella and does not exhibit cross-reactivity of greater than 10% with *Deightoniella torulosa, Cladosporium herbarum, Cladosporium musae, Dreschlera gigantea, Fusarium oxysporium,* and *Rhizopus stolonifer.*

2. The hybridoma cell line of claim 1 wherein at least one species is selected from the group consisting of *M. fijiensis* var *difformis, M. graminicola* and *M. musicola.*

3. The hybridoma cell line of claim 1 wherein said antibody binds more than one species of Mycosphaerella.

4. The hybridoma cell line of claim 2 which is deposited with the American Type Culture Collection as ATCC HB 10186.

5. The hybridoma cell line of claim 3 which is deposited with the American Type Culture Collection as ATCC HB 10413.

6. The hybridoma cell line of claim 3 which is deposited with the American Type Culture Collection as ATCC HB 10414.

7. A monoclonal antibody which binds with at least one species of Mycosphaerella and does not exhibit cross-reactivity of greater than 10% with *Deightoniella torulosa, Cladosporium herbarum, Cladosporium musae, Dreschlera gigantea, Fusarium oxysporium,* and *Rhizopus stolonifer.*

8. The antibody of claim 7 wherein at least one species is selected from the group consisting of *M. fijiensis* var *difformis, M. graminicola* and *M. musicola.*

9. The antibody of claim 7 wherein said antibody binds more than one species of Mycosphaerella.

10. The antibody of claim 8 wherein said antibody is produced by a hybridoma which is deposited with the American Type Culture Collection as ATCC HB 10186.

11. The antibody of claim 9 wherein said antibody is produced by a hybridoma which is deposited with the American Type Culture Collection as ATCC HB 10413.

12. The antibody of claim 9 wherein said antibody is produced by a hybridoma which is deposited with the American Type Culture Collection as ATCC HB 10414.

13. The antibody of claim 9 which is produced in response to an extract of mycelia or conidia of *Mycosphaerella fijiensis.*

14. A method for detecting the presence of absence of Mycosphaerella in a sample suspected of containing Mycosphaerella antigens which comprises:

(a) contacting the sample with at least one monoclonal antibody that binds with at least one species of Mycosphaerella and does not exhibit cross-reactivity of greater than 10% with *Deightoniella torulosa, Cladosporium herbarum, Cladosporium musae, Dreschlera gigantea, Fusarium oxysporium,* and *Rhizopus stolonifer*; and (b) observing the presence of absence of an antibody-antigen binding reaction.

15. A method for detecting the presence of absence of Mycosphaerella in a sample suspected of containing Mycosphaerella antigens which comprises:

(a) contacting the sample with two monoclonal antibodies that bind with at least one species of Mycosphaerella and do not exhibit cross-reactivity of greater than 10% with *Deightoniella torulosa, Cladosporium herbarum, Cladosporium musae, Dreschlera gigantea, Fusarium oxysporium,* and *Rhizopus stolonifer* wherein one of said antibodies is immobilized and the other of the antibodies is labeled with a reporter molecule; and (b) observing the presence of absence of an antibody-antigen binding reaction.

16. The method of claim 14 wherein the at least one species is selected from the group consisting of *M. fijiensis* var *difformis*, *M. graminicola* and *M. musicola*.

17. The method of claim 15 wherein at least one of the antibodies binds at least one species selected from the group consisting of *M. fijiensis* var *difformis*, *M. graminicola* and *M. musicola*.

18. The method of claim 14 wherein the antibody binds more than one species of Mycosphaerella.

19. The method of claim 15 wherein at least one of the antibodies binds with more than one species of Mycosphaerella.

20. The antibody of claim 16 wherein said antibody is produced by a hybridoma which is deposited with the American Type Culture Collection as ATCC HB 10186.

21. The method of claim 17 wherein said antibody is produced by a hybridoma which is deposited with the American Type Culture Collection as ATCC HB 10186.

22. The method of claim 18 wherein said antibody is produced by a hybridoma which is deposited with the American Type Culture Collection as ATCC HB 10413.

23. The method of claim 19 wherein said antibody is produced by a hybridoma which is deposited with the American Type Culture Collection as ATCC HB 10413.

24. The method of claim 18 wherein said antibody is produced by a hybridoma which is deposited with the American Type Culture Collection as ATCC HB 10414.

25. The method of claim 19 wherein said antibody is produced by a hybridoma which is deposited with the American Type Culture Collection as ATCC HB 10414.

26. A diagnostic kit comprising a first anti-Mycosphaerella antibody bound to a solid support and a second anti-Mycosphaerella antibody labeled with reporter molecule, wherein at least one of said antibodies is a monoclonal antibody that binds with at least one species of Mycosphaerella and does not exhibit cross-reactivity of greater than 10% with *Deightoniella torulosa*, *Cladosporium herbarum*, *Cladosporium musae*, *Dreschlera gigantea*, *Fusarium oxysporium*, and *Rhizopus stolonifer*.

27. The kit of claim 26 wherein said monoclonal antibody binds at least one species selected from the group consisting of *M. fijiensis* var *difformis*, *M. graminicola* and *M. musicola*.

28. The kit of claim 26 wherein said monoclonal antibody binds more than one species of Mycosphaerella.

29. The kit of claim 26 wherein said monoclonal antibody is produced by a hybridoma which is deposited with the American Type Culture Collection as ATCC HB 10186.

30. The kit of claim 28 wherein said monoclonal antibody is produced by a hybridoma which is deposited with the American Type Culture Collection as ATCC HB 10413.

31. The kit of claim 28 wherein said monoclonal antibody is produced by a hybridoma which is deposited with the American Type Culture Collection as ATCC HB 10414.

32. The kit of claim 26 wherein the reporter molecule is an enzyme.

33. The kit of claim 32 further comprising a substrate specific for the enzyme.

* * * * *